(12) United States Patent
Quaid

(10) Patent No.: US 8,361,163 B2
(45) Date of Patent: Jan. 29, 2013

(54) PROSTHETIC DEVICE AND SYSTEM FOR PREPARING A BONE TO RECEIVE A PROSTHETIC DEVICE

(75) Inventor: Arthur E. Quaid, Fort Lauderdale, FL (US)

(73) Assignee: Mako Surgical Corp., Ft. Lauderdale, FL (US)

( * ) Notice: Subject to any disclaimer, the term of this patent is extended or adjusted under 35 U.S.C. 154(b) by 398 days.

(21) Appl. No.: 12/330,271

(22) Filed: Dec. 8, 2008

(65) Prior Publication Data

US 2009/0149965 A1 Jun. 11, 2009

Related U.S. Application Data

(60) Provisional application No. 61/007,033, filed on Dec. 10, 2007, provisional application No. 61/005,990, filed on Dec. 10, 2007.

(51) Int. Cl.
*A61F 2/36* (2006.01)
(52) U.S. Cl. .................................. 623/23.12; 623/23.13
(58) Field of Classification Search ..... 623/23.12–23.14
See application file for complete search history.

(56) References Cited

U.S. PATENT DOCUMENTS

| | | | |
|---|---|---|---|
| 4,005,495 A | 2/1977 | Locke et al. | |
| 4,224,699 A | 9/1980 | Weber | |
| 5,405,389 A | 4/1995 | Conta et al. | |
| 5,800,557 A | 9/1998 | Elhami | |
| 6,758,864 B2 | 7/2004 | Storer et al. | |
| 6,866,685 B2 | 3/2005 | Chan et al. | |
| 7,206,626 B2 | 4/2007 | Quaid, III | |
| 7,255,717 B2 | 8/2007 | Park et al. | |
| 2003/0055501 A1* | 3/2003 | Fell et al. | 623/14.12 |
| 2003/0163202 A1 | 8/2003 | Lakin | |
| 2003/0187514 A1 | 10/2003 | McMinn | |
| 2005/0085915 A1* | 4/2005 | Steinberg | 623/17.16 |
| 2005/0256585 A1 | 11/2005 | Park et al. | |
| 2006/0142657 A1 | 6/2006 | Quaid et al. | |
| 2006/0241779 A1 | 10/2006 | Lakin | |
| 2007/0260256 A1 | 11/2007 | Beaule | |
| 2009/0149965 A1 | 6/2009 | Quaid | |
| 2009/0157192 A1 | 6/2009 | Stuart | |

FOREIGN PATENT DOCUMENTS

| | | |
|---|---|---|
| CH | 626249 A5 | 11/1981 |
| DE | 976768 C | 4/1964 |
| DE | 25 24 923 B1 | 11/1976 |
| DE | 27 42 464 A1 | 3/1979 |
| DE | 101 30 366 A1 | 11/2002 |
| DE | 2020060 17 005 U1 | 1/2007 |

(Continued)

OTHER PUBLICATIONS

International Search Report from corresponding PCT application No. PCT/US2008/085898 (2 pages.).

(Continued)

*Primary Examiner* — Thomas J Sweet
*Assistant Examiner* — Jason-Dennis Stewart
(74) *Attorney, Agent, or Firm* — Foley & Lardner LLP

(57) ABSTRACT

A substantially cup-shaped prosthetic device for a joint is provided. The prosthetic device includes an outer surface configured to operatively engage at least one of a first bone of the joint and a component and an inner surface configured to connect to a second bone of the joint. The inner surface is rotationally asymmetric to minimize intrusion on a vascular region of the second bone.

12 Claims, 14 Drawing Sheets

FOREIGN PATENT DOCUMENTS

| | | |
|---|---|---|
| EP | 0 840 94 A1 | 7/1983 |
| EP | 1 570 811 A1 | 9/2005 |
| EP | 1 611 870 A1 | 1/2006 |
| FR | 2391712 A1 | 11/1976 |
| GB | 718 935 A | 11/1954 |
| WO | WO-89/11873 | 12/1989 |

OTHER PUBLICATIONS

International Search Report and Written Opinion issued in related International Patent Application No. PCT/US2008/085880, completed Mar. 3, 2009.

* cited by examiner

PROSTHETIC DEVICE AND SYSTEM FOR PREPARING A BONE TO RECEIVE A PROSTHETIC DEVICE

CROSS-REFERENCE TO RELATED APPLICATIONS

The present application claims priority to U.S. Provisional Patent Application Ser. No. 61/007,033, filed Dec. 10, 2007, and U.S. Provisional Patent Application Ser. No. 61/005,990, filed Dec. 10, 2007, each of which is hereby incorporated by reference herein in its entirety.

BACKGROUND OF THE INVENTION

1. Field of the Invention

The invention relates to orthopedic joint replacement and, more particularly, to a prosthetic device for use in orthopedic joint replacement and a system for preparing a bone to receive the prosthetic device.

2. Description of Related Art

FIG. 1A illustrates the bones of a hip joint 10, which include a portion of a pelvis 12 and a proximal end of a femur 14. The proximal end of the femur 14 has a superior aspect 14a and an inferior aspect 14b and includes a ball shaped part called the femoral head 16. The femoral head 16 is disposed on a femoral neck 18, which is connected to a femur shaft 20. As shown in FIG. 1B, the femoral head 16 fits into a concave socket in the pelvis 12 called the acetabulum 22, forming the hip joint 10. The acetabulum 22 and femoral head 16 are both covered by articular cartilage that absorbs shock and promotes articulation of the joint 10. Additionally, as shown in FIG. 1C, the superior aspect 14a of the proximal end of the femur 14 includes a vascular region 24 having a high concentration of retinacular vessels 24a located near or on the surface of the bone of the femoral head 16 and neck 18. The retinacular vessels 24a supply blood to the bone tissue of the femoral head 16.

Over time, the hip joint 10 may degenerate (for example, due to osteoarthritis) resulting in pain and diminished functionality. To reduce pain and restore functionality, a hip replacement procedure, such as total hip arthroplasty or hip resurfacing, may be necessary. During hip replacement, a surgeon replaces portions of a patient's hip joint 10 with artificial components. In conventional total hip arthroplasty, the surgeon removes the femoral head 16 and neck 18 (shown in FIG. 2A) and replaces the natural bone with a prosthetic femoral component 26 comprising a head 26a, a neck 26b, and a stem 26c (shown in FIG. 2B). As shown in FIG. 2C, the stem 26c of the femoral component 26 is anchored in a cavity that the surgeon creates in the intramedullary canal of the femur 14. Similarly, if the natural acetabulum 22 of the pelvis 12 is worn or diseased, the surgeon reams the acetabulum 22 and replaces the natural surface with a prosthetic acetabular component 28 comprising a hemispherical shaped cup 28a (shown in FIG. 2B) that may include a liner 28b. In cases where the acetabulum 22 is healthy, the surgeon may leave the natural acetabulum 22 intact and replace only the femoral head 16 and neck 18.

In contrast to total hip arthroplasty, which is highly invasive, patients who have healthy subsurface bone and disease that is confined to the surface of the femoral head 16 may be candidates for hip resurfacing. In conventional hip resurfacing, the surgeon removes diseased bone from the femoral head 16 using a rotationally symmetric cutting tool, such as a cylindrical reamer 30. As shown in FIG. 3A, the surgeon centers the cylindrical reamer 30 on an axis A-A defined by a guide hole G created in the femoral head 16. In operation, the cutting element of the cylindrical reamer 30 rotates about the femoral head 16 cutting away diseased surface bone and resulting in a femoral head 16 having a rotationally symmetric surface shape 16a. As shown in FIGS. 3B and 3C, the reamed femoral head is mated with a prosthetic femoral head cup 32. The femoral head cup 32 typically has an internal surface shape that substantially corresponds to the rotationally symmetric surface shape 16a of the reamed femoral head so that the cup 32 will fit securely in place. The femoral head cup 32 also includes a central stem 32a that is received in the guide hole G to aid in alignment and stability of the femoral head cup 32. As with conventional hip arthroplasty, hip resurfacing may include replacement of the acetabulum 22 when the natural acetabulum 22 is damaged or diseased.

As can be seen by comparing FIGS. 2C and 3B, hip resurfacing is less invasive and preserves more bone than conventional hip arthroplasty because only a portion of the femoral head 16 is removed leaving the femoral neck 18, the subsurface bone of the femoral head 16, and the intramedullary canal of the femur 14 intact. Although conventional hip resurfacing removes less bone than conventional hip arthroplasty, the procedure still removes a significant portion of the femoral head 16, including healthy bone. As shown in FIG. 3D, one consequence of the conventional resurfacing process is that the bone cuts can impinge upon the vascular region 24 of the femur 14 resulting in damage to the retinacular vessels 24a. This damage adversely impacts the blood supply to the femoral head 16, which can ultimately lead to necrosis of the bone, loosening of the implanted femoral head cup 32, pain, and femoral fracture. Additionally, if the cylindrical reamer 30 is undersized or malpositioned, there is a danger of the cylindrical reamer 30 contacting the femoral neck 18, creating a notch in the femoral neck 18. This femoral "notching" causes a stress riser in the femur 14 that increases the risk of femoral fracture, particularly if the notching occurs on the superior aspect 14a of the femoral neck 18, which is in tension during activities such as standing, walking, and running.

SUMMARY OF THE INVENTION

According to an aspect of the present invention, a substantially cup-shaped prosthetic device for a joint includes an outer surface configured to operatively engage at least one of a first bone of the joint and a component and an inner surface configured to connect to a second bone of the joint. The inner surface is rotationally asymmetric to minimize intrusion on a vascular region of the second bone.

According to another aspect, a robotic system for preparing a bone of a joint to receive a substantially cup-shaped prosthetic device includes a controllable guide structure configured to guide cutting of the bone into a shape for receiving the substantially cup-shaped prosthetic device and a control system for controlling the guide structure. The control system defines a bone-cutting pattern configured to minimize intrusion on a vascular region of the bone.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION OF PREFERRED EMBODIMENTS

Figure 1A:
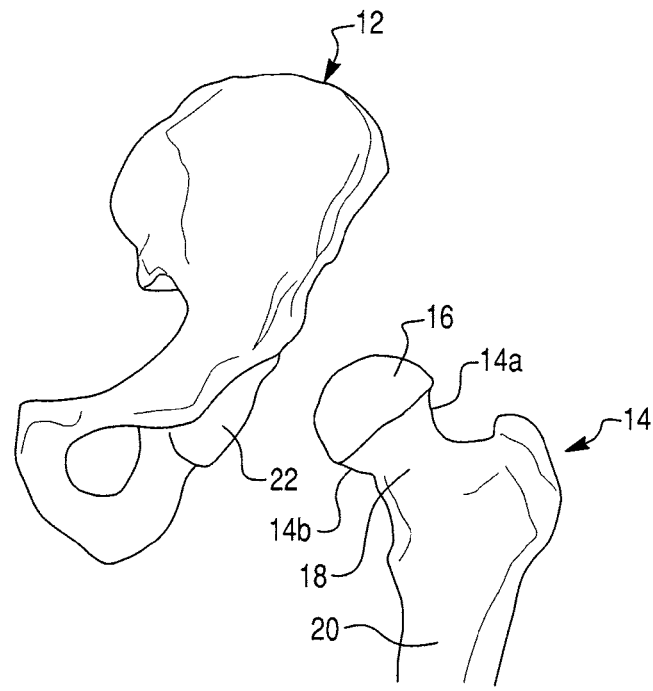
FIG. 1A is a perspective view of a femur and a pelvis.

Presently preferred embodiments of the invention are illustrated in the drawings. An effort has been made to use the same or like reference numbers throughout the drawings to refer to the same or like parts.

FIGS. 4A through 4F show an embodiment of a prosthetic device 5 according to the present invention. In this embodiment, the prosthetic device 5 is a femoral hip implant (e.g., a femoral head cup). The present invention, however, is not limited to hip implants. The prosthetic device may be any cup-shaped orthopedic joint implant, such as an implant for resurfacing a portion of a ball and socket joint (e.g., a hip or shoulder joint). In the alternative, the prosthetic device may be a trial of an implant. As used herein, the term cup-shaped means having a generally convex outer surface and a generally concave inner surface, though the surfaces need not be continuous.

As shown in FIGS. 4A through 4F, the prosthetic device 5 is substantially cup-shaped and includes an outer surface 50 and an inner surface 60. The prosthetic device 5 may optionally include a stem 55. The prosthetic device 5 is designed to replace a portion of a joint that includes a first bone (e.g., the acetabulum 22 of the pelvis 12) and a second bone (e.g., the femoral head 16 of the femur 14). In particular, as with a conventional hip resurfacing femoral implant (such as the femoral head cup 32 shown in FIG. 3C), the prosthetic device 5 is designed to be implanted on the proximal end of the femur 14 to restore functionality to the joint 10 in cases where the femoral head 16 is compromised, e.g., its surface is damaged or diseased.

Figure 2A:
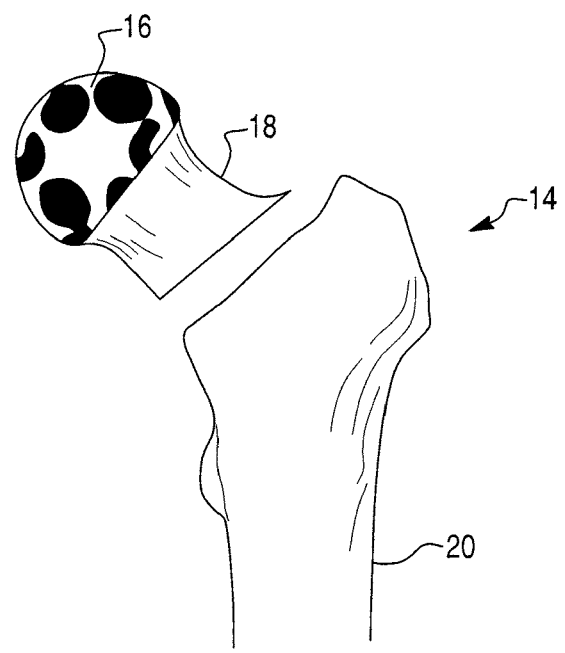
FIG. 2A is a perspective view of a bone cut made during a conventional total hip replacement procedure.
Figure 2B:
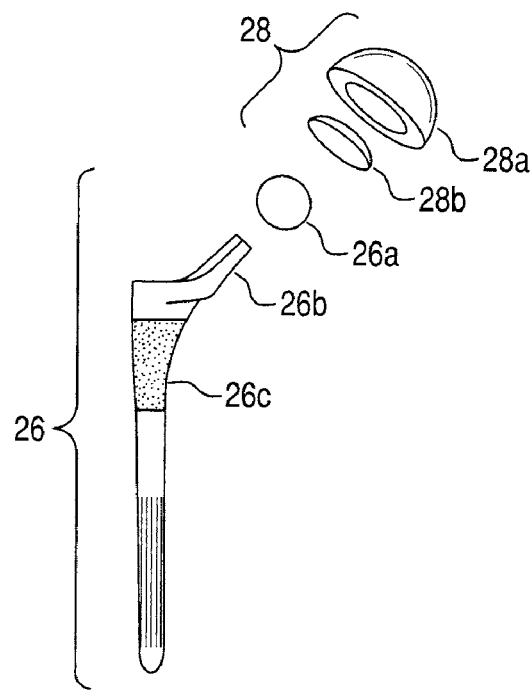
FIG. 2B is a perspective view of a femoral component and an acetabular component for a conventional total hip replacement procedure.
Figure 2C:
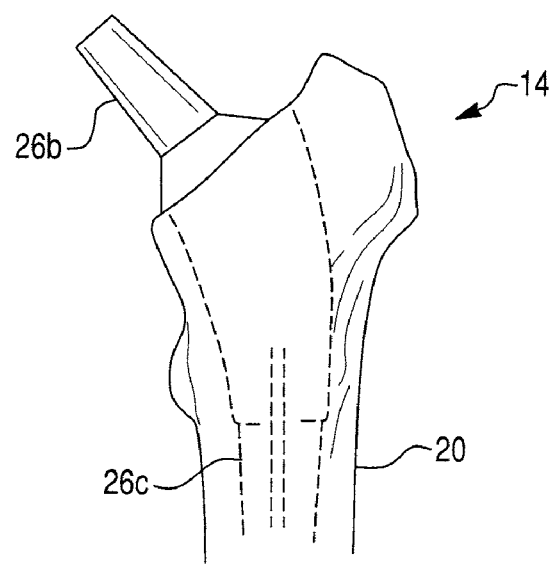
FIG. 2C is a perspective view of the femoral component of FIG. 2B implanted in a femur.
Figure 4A:
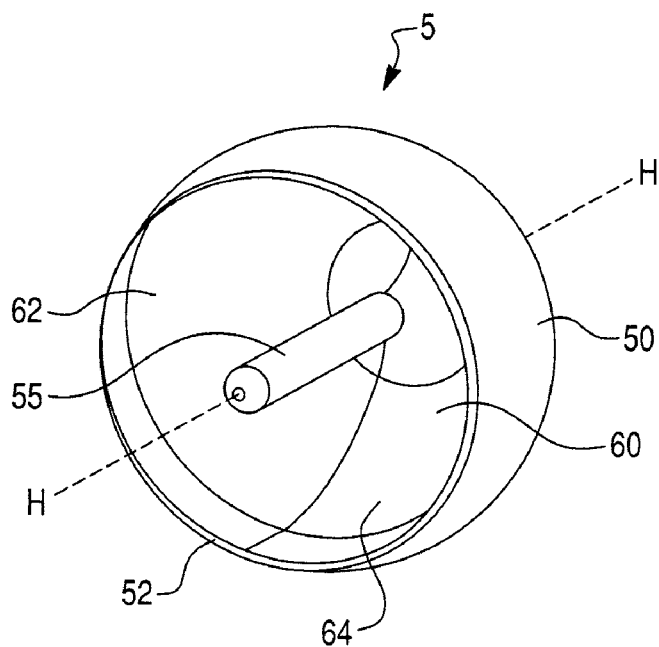
FIG. 4A is a perspective view of an embodiment of prosthetic device according to the present invention.

The outer surface 50 of the prosthetic device 5 is configured to replace the surface of the femoral head 16. Thus, when the prosthetic device 5 is implanted in a patient, the outer surface 50 forms one articular surface of the hip joint 10. The other articular surface is formed either by the natural acetabulum 22 or by an acetabular component implanted in the hip joint 10 (such as the acetabular component 28 shown in FIG. 2B). As shown in FIGS. 4C and 4D, the outer surface 50 preferably is convex and substantially shaped in the form of a sphere with the bottom portion of the sphere being truncated by a plane T-T so that the outer surface 50 terminates at an edge 52. An axis H-H passes through the geometric center of the sphere and is oriented to be perpendicular to the plane T-T. To enable articulation, the outer surface 50 can be manufactured with high sphericity and surface smoothness to minimize friction and wear, in accordance with parameters known in the art. In this manner, the outer surface 50 is configured to operatively engage (or articulate with) at least one of a first bone of a joint 10 (e.g., the acetabulum 22) and a component implanted in the joint 10 (e.g., the acetabular component 28).

Figure 3A:
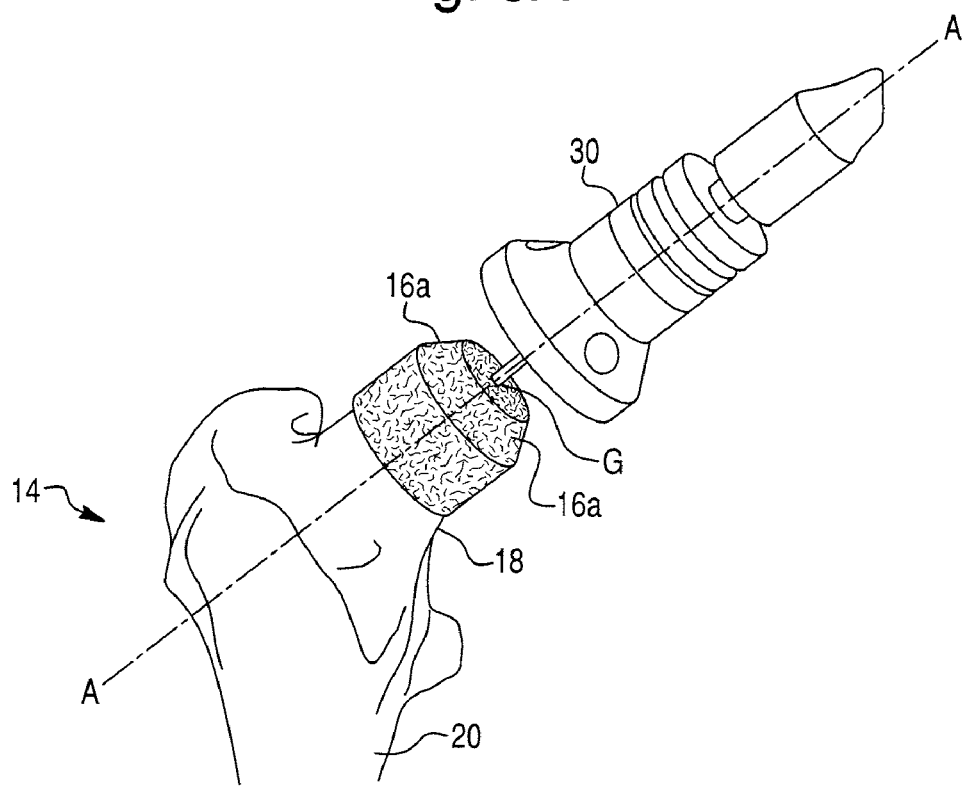
FIG. 3A is a perspective view of rotationally symmetric bone cuts made with a cylindrical reamer during a conventional hip resurfacing procedure.
Figure 3B:
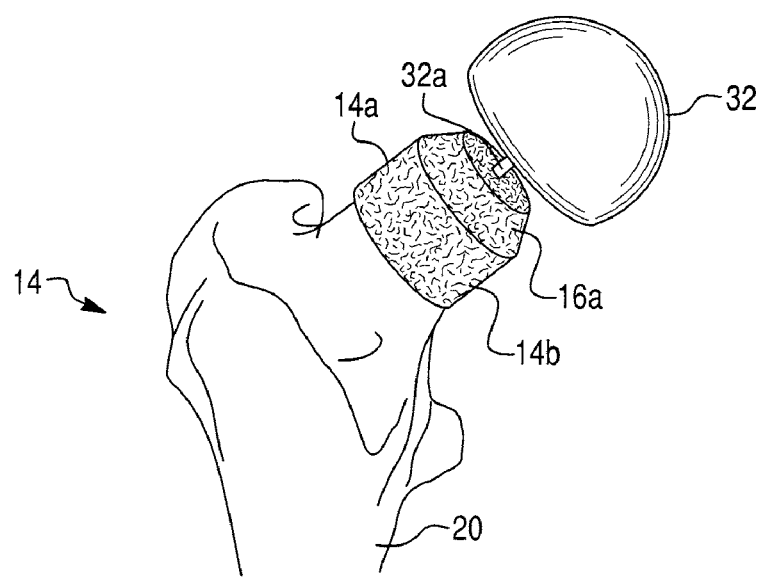
FIG. 3B is a perspective view of a femoral component for a conventional hip resurfacing procedure.
Figure 4B:
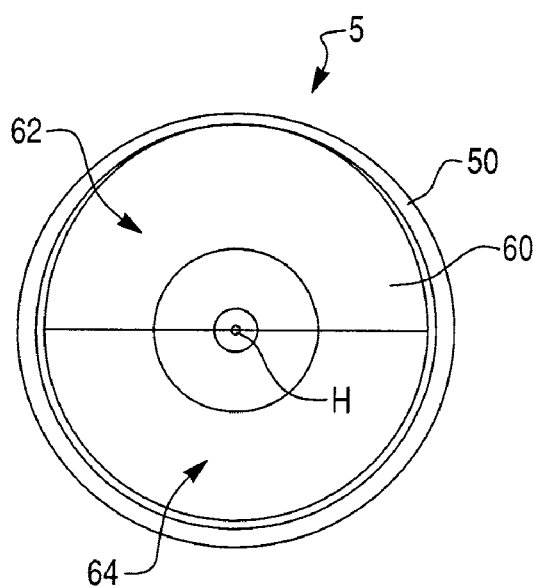
FIG. 4B is a bottom plan view of the prosthetic device of FIG. 4A.
Figure 4C:
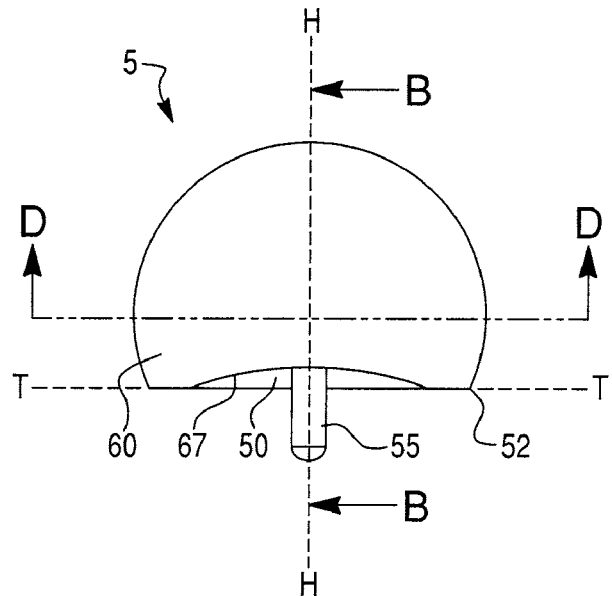
FIGS. 4C and 4D are side elevation views of the prosthetic device of FIG. 4A.
Figure 4D:
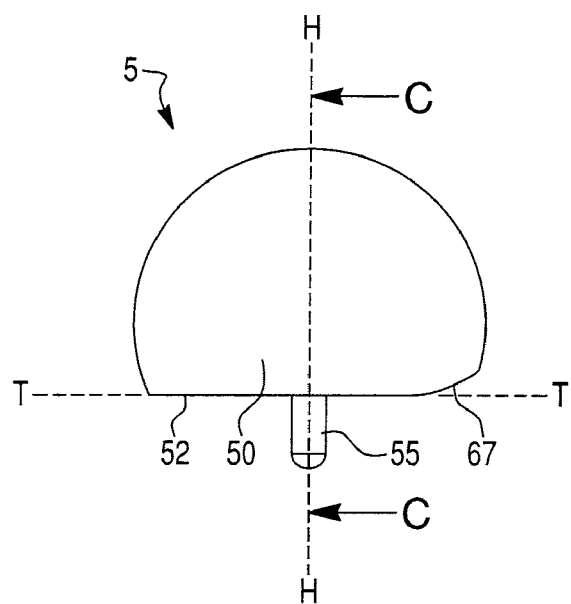
Figure 4E:
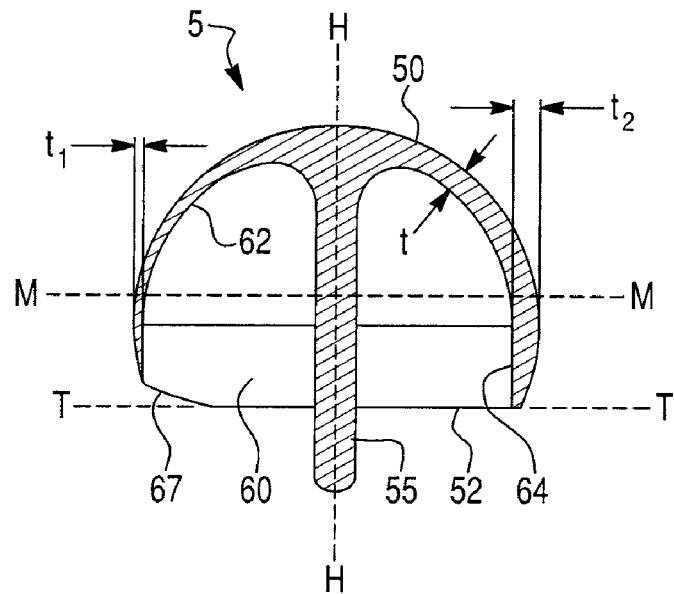
FIGS. 4E and 4F are cross sectional views of the prosthetic device of FIGS. 4A-4D.
Figure 4F:
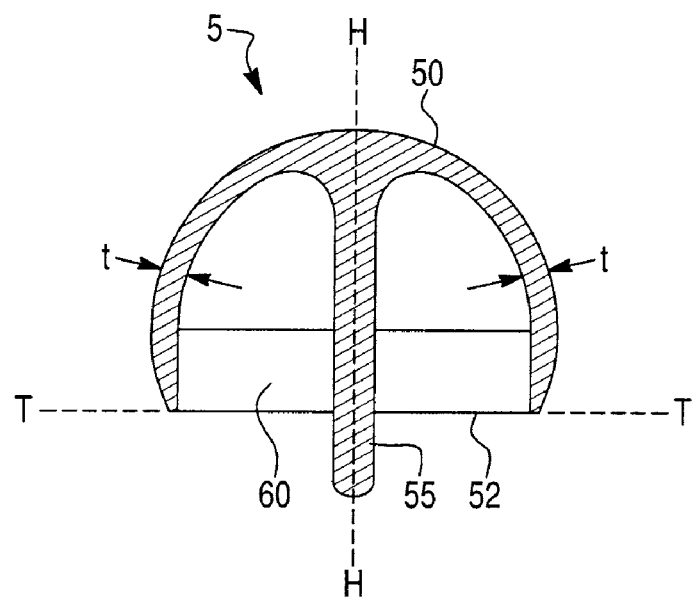

The inner surface 60 of the prosthetic device 5 is separated from the outer surface 50 by a wall thickness t and, like the outer surface 50, terminates at the edge 52 as shown in FIGS. 4E and 4F. Similar to a conventional femoral resurfacing implant, the inner surface 60 is configured to abut the surface of the femoral head 16 when the prosthetic device 5 is implanted on the femur 14. However, unlike the conventional femoral head cup 32 (shown in FIG. 3B), which has an inner surface that is rotationally symmetric about the central axis of the stem 32a to enable the cup 32 to mate with a femoral head 16 that has been prepared using rotationally symmetric cutting tools (such as the cylindrical reamer 30 shown in FIG. 3B), the inner surface 60 of the prosthetic device 5 is rotationally asymmetric to minimize (or reduce) intrusion on critical regions of anatomy, such as the vascular region 24. As used herein, the term rotationally symmetric means correspondence of shape about an axis. An example of an object having rotational symmetry is a surface of revolution, which is generated by rotating a two dimensional curve about an axis. For example, a cylinder, a spheroid, and a cone are all surfaces of revolution. Similarly, the surface shape 16a shown in FIGS. 3A and 3B is a surface of revolution about the axis A-A. In contrast, "rotationally asymmetric" means lacking correspondence of shape about an axis. In the case of the prosthetic device 5, for example, the shape of the inner surface 60 is rotationally asymmetric about the axis H-H shown in FIGS. 4C-4F.

The rotationally asymmetric shape of the inner surface 60 advantageously enables the surgeon to preserve healthy bone and critical anatomical structures, such as the retinacular vessels 24a located in the vascular region 24. This may be accomplished, for example, by reducing the amount of bone that needs to be resected in a critical region and/or sculpting the bone into a shape that avoids critical structures. For example, the prosthetic device 5 may be configured so that the inner surface 60 has a shape that promotes targeted bone conservation, meaning that the shape of the inner surface 60 enables the surgeon to fit the prosthetic device 5 to the femur 14 without having to cut away as much bone from specified critical regions as would be required for a conventional resurfacing implant (such as the femoral head cup 32 shown in FIG. 3B). For example, an appropriately sized elliptical or ellipsoid shape may require less bone resection in critical regions than a conventional circular, cylindrical, or spherical shape.

Figure 3C:
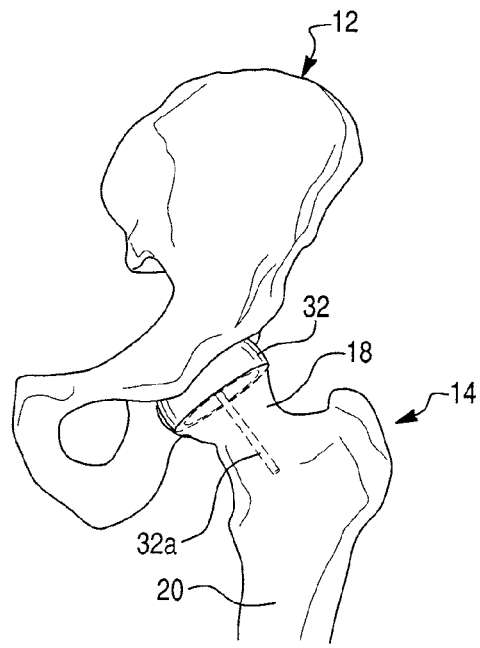
FIG. 3C is a perspective view of the femoral component of FIG. 3B implanted on a femur of a hip joint.
Figure 3D:
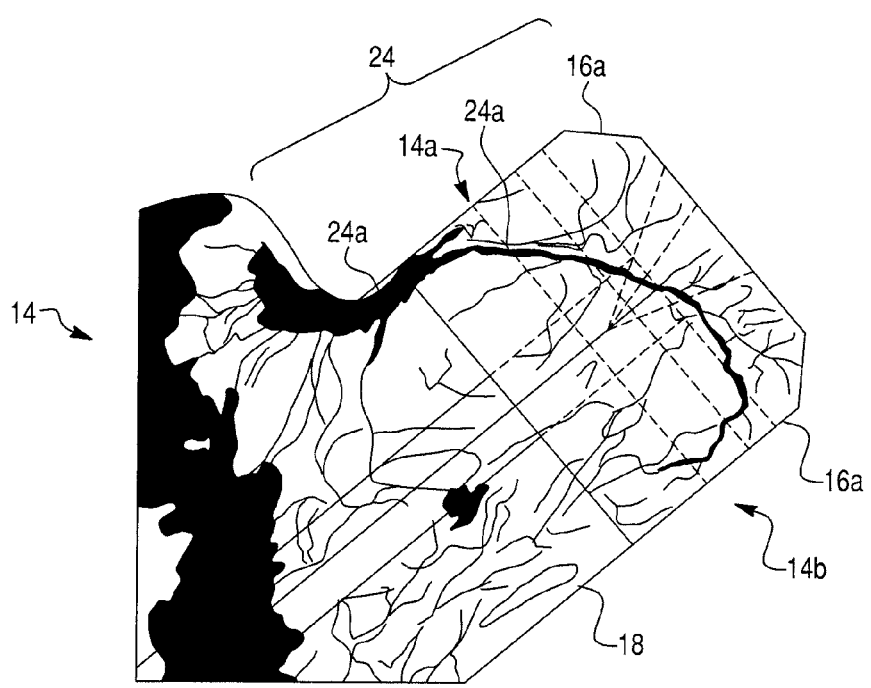
FIG. 3D is an illustration depicting the vascular region of FIG. 1C in relation to rotationally symmetric bone cuts made with a cylindrical reamer during a conventional hip resurfacing procedure.
Figure 5A:
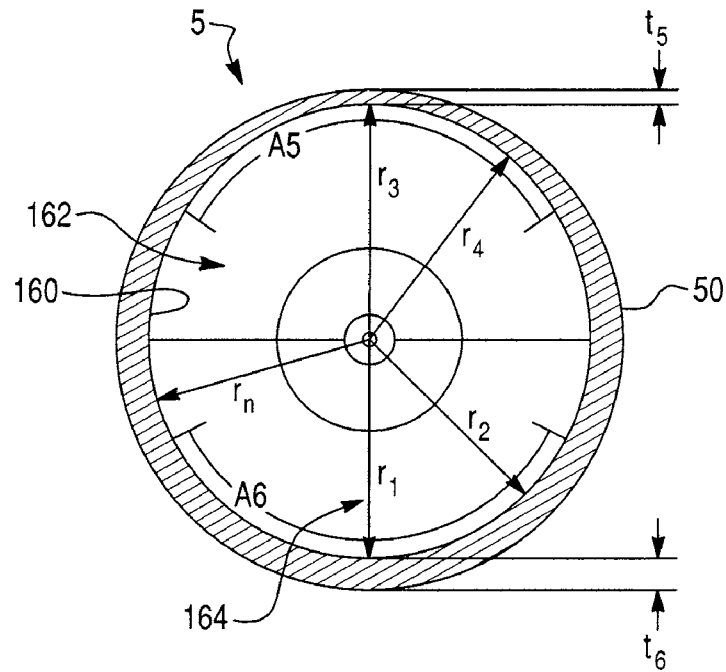
FIGS. 5A and 5B are cross sectional views of an embodiment of a prosthetic device according to the present invention.
Figure 5B:
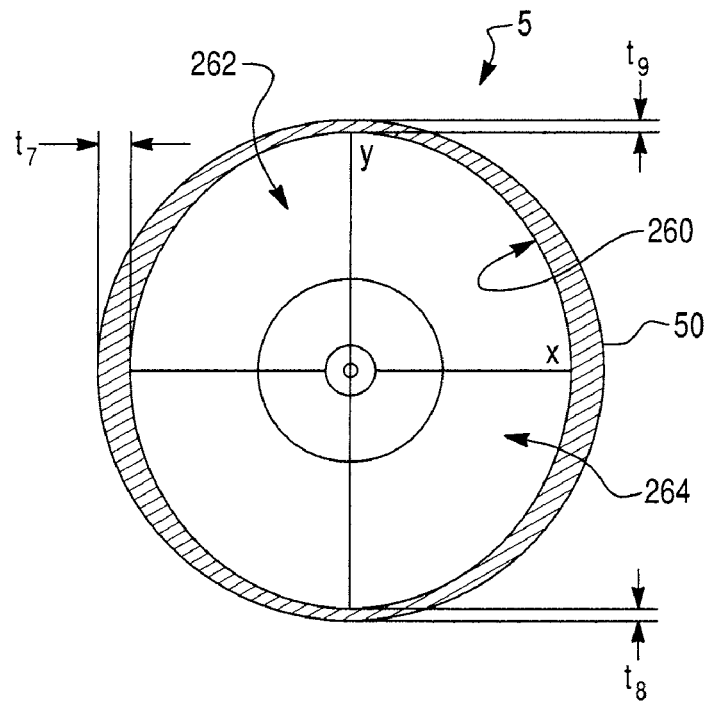

As an illustration, according to an embodiment, the inner surface 60 of the prosthetic device 5 has an oval (or elliptical) shape with the bone-conserving portions located at each end of the major axis Y (i.e., the long axis) of the oval. An example of this embodiment is shown in FIG. 5B, which is a cross sectional view of the prosthetic device 5 taken along the line D-D shown in FIG. 4C. In this embodiment, the prosthetic device 5 includes an inner surface 260 that corresponds to the inner surface 60 shown in FIGS. 4A-4F. In this case, when cutting bone, instead of using a cylindrical reamer to cut the femoral head 16 into a conventional rotationally symmetric cylindrical shape (as shown in FIGS. 3B and 3D), the surgeon uses a cutting tool such as a high speed burr, for example, to sculpt the femoral head 16 into a rotationally asymmetric oval (or elliptical) shape corresponding to the rotationally asymmetric oval shape of the inner surface 60. Thus, the sculpted bone has convex surfaces substantially corresponding in shape to the concave surfaces of the inner surface 60 to enable the prosthetic device 5 to engage the sculpted bone. To conserve bone in the vascular region 24 of the femur 14, the surgeon sculpts the femoral head 16 such that the long axis of the sculpted oval is oriented in the direction of the superior and inferior aspects 14a and 14b of the femur 14. Sculpting the bone in this manner advantageously requires less bone resection radially. Thus, significant impingement of the cutting tool on the critical vascular region 24 is avoided. As a result, there is a reduced likelihood that the retinacular vessels 24a below the surface of the bone will be damaged and a reduced likelihood that the femoral neck 20 will be inadvertently notched. When implanting the prosthetic device 5, the surgeon aligns the major axis Y of the inner surface 60 with the long axis of the oval of the sculpted bone. Thus, the bone-conserving portions of the prosthetic device 5 are collocated with the preserved portions of the femur 14. In this manner, the rotational asymmetry of the inner surface 60 minimizes intrusion of the prosthetic device 5 on the vascular region 24 so that healthy bone and critical anatomical structures are protected and preserved.

As shown in FIG. 4B, the inner surface 60 of the prosthetic device 5 includes a bone-engaging first concave surface 62 and a bone-engaging second concave surface 64. When the prosthetic device 5 is implanted on the femoral head 16, the surfaces 62 and 64 abut the bone and/or a cement mantle used to promote fixation of the prosthetic device 5. Any portion of the inner surface 60 may be configured to promote bone conservation in one or more critical regions of anatomy. Thus, the bone-conserving portion of the inner surface 60 may include the surface 62 (in whole or in part), the surface 64 (in whole or in part), and/or any other portion of the inner surface 60.

Figure 5C:
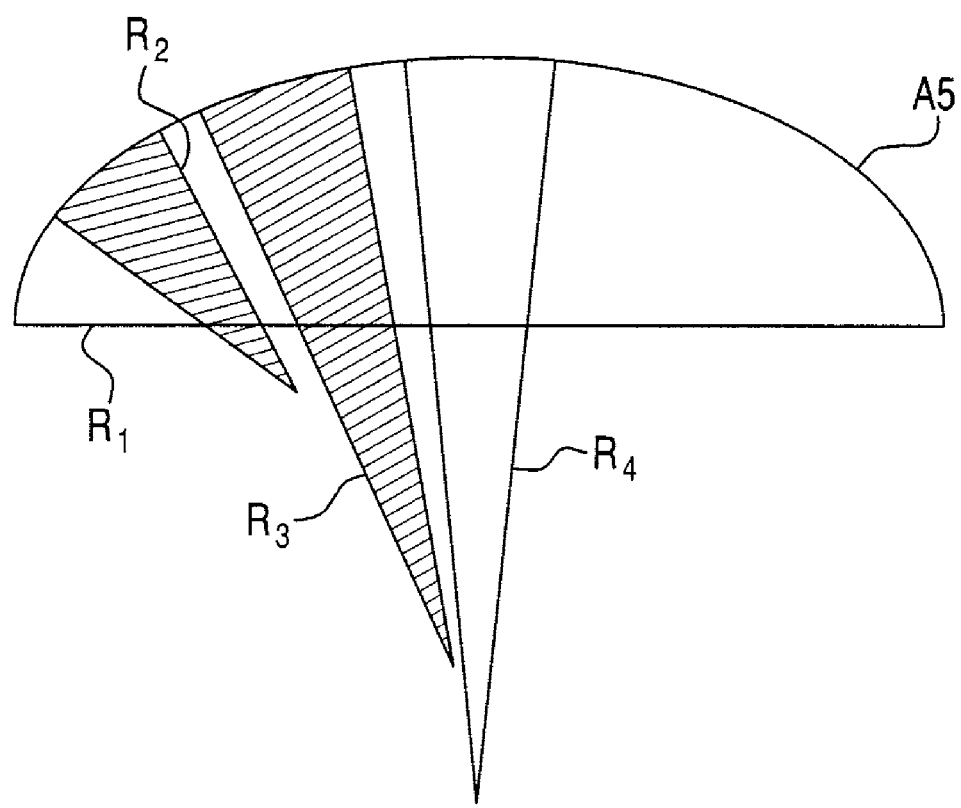
FIG. 5C shows a portion of the cross sectional view of FIG. 5A.

In one embodiment, a shape of the first concave surface 62 is different from a shape of the second concave surface 64. For example, FIG. 5A shows a cross sectional view of the prosthetic device 5 taken along the line D-D shown in FIG. 4C. In this embodiment, the prosthetic device 5 includes an inner surface 160 that corresponds to the inner surface 60 shown in FIGS. 4A-4F. The inner surface 160 includes a bone-engaging first concave surface 162 and a bone-engaging second concave surface 164. As shown in FIG. 5A, the cross section at the first concave surface 162 has a semi-elliptical shape (i.e., half of an ellipse or oval), and the cross section at the second concave surface 164 has a semi-circular shape (i.e., half of a circle). Thus, in the embodiment of FIG. 5A, a cross section of the inner surface 160 includes both an elliptical arc A5 (along the first concave surface 162) and a circular arc A6 (along the second concave surface 164). A circle has a constant radius and constant radius of curvature. Thus, the second concave surface 164 has a substantially constant radius and constant radius of curvature (e.g., radius $r_1$, radius $r_2$, and radius $r_n$ are equal). In contrast, the radius and radius of curvature of an ellipse are non-constant with the radius of an ellipse varying from a maximum along the semimajor axis of the ellipse to a minimum along the semiminor axis of the ellipse. Thus, the first concave surface 162 has a radius that varies (e.g., radius $r_3$ and radius $r_4$ are not equal) and a non-constant radius of curvature (e.g., as shown in FIG. 5C, radius of curvature $R_1$, radius of curvature $R_2$, radius of curvature $R_3$, and radius of curvature $R_4$ are not equal). Additionally, because the first and second surfaces 162 and 164 have different shapes, the first surface 162 has at least one radius (e.g., the radius $r_1$) that is different from a radius of the second surface 164 (e.g., the radius $r_4$). One advantage of an inner surface 160 that includes a semi-ellipse on one half of the inner surface 60 and a semi-circle on the other half is that such a configuration provides smooth transitions between the two halves and reduces stress risers in the prosthetic device 5, the resected bone of the femur 14, and the bone cement (if used for fixation).

Figure 6A:
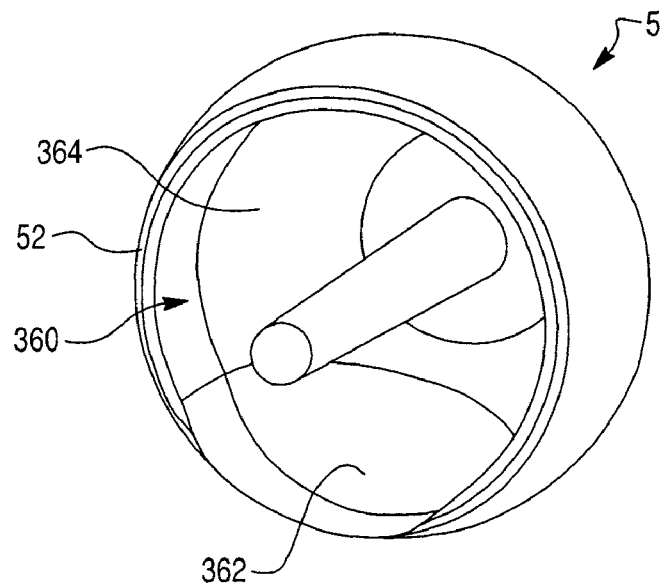
FIG. 6A is a perspective view of an embodiment of prosthetic device according to the present invention.
Figure 6B:
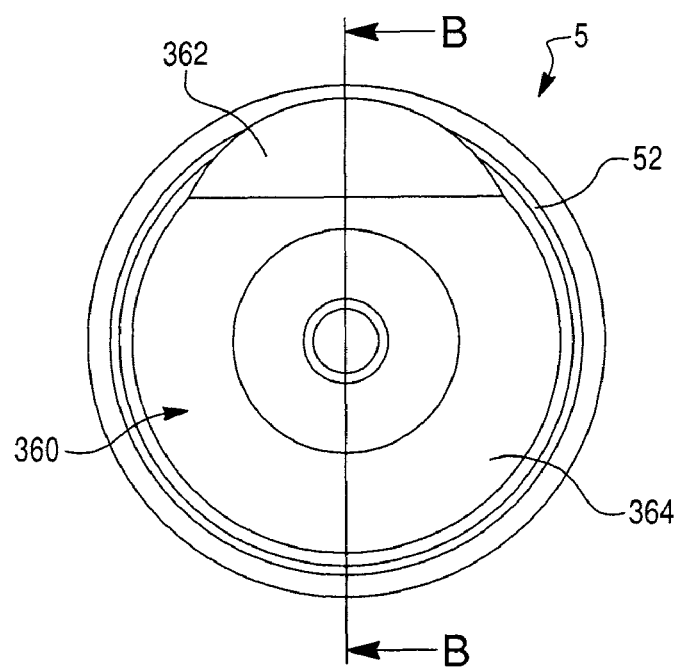
FIG. 6B is a bottom plan view of the prosthetic device of FIG. 6A.
Figure 6C:
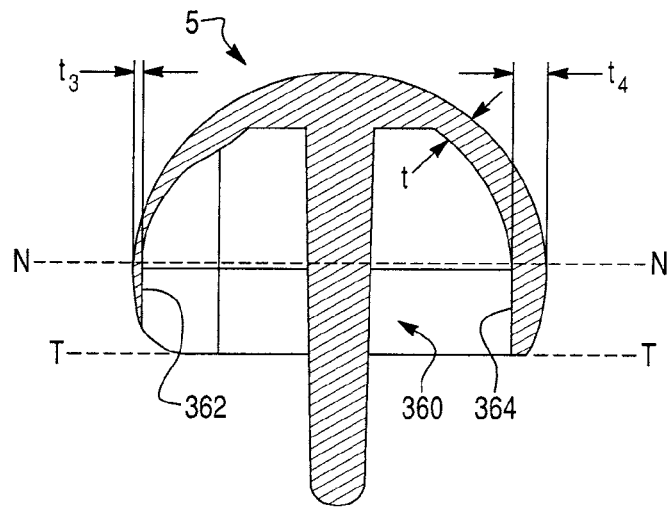
FIGS. 6C is a cross sectional view of the prosthetic device of FIGS. 6A and 6B.

In another embodiment, the prosthetic device 5 includes an inner surface 360 (shown in FIGS. 6A-6C) that corresponds to the inner surface 60 of FIGS. 4A-4F. The inner surface 360 includes a bone-engaging first concave surface 362 and a bone-engaging second concave surface 364. As in the previous embodiment, the first and second concave surfaces 362 and 364 have different shapes. As shown in FIGS. 6A-6C, the second concave surface 364 has a larger surface area and a different curvature than the first concave surface 362. For example, the surface 364 may comprise a circular arc (as discussed above in connection with FIG. 5A), and the surface 362 may comprise an elliptical arc (as discussed above in connection with FIG. 5A). One advantage of the embodiment of FIGS. 6A-6C over the embodiment of FIG. 5A is that the area of the surface 362 is smaller than the area of the surface 162, which results in a prosthetic device 5 having more material and thus increased strength and stiffness. One drawback, however, is that the embodiment of FIGS. 6A-6C provides a less continuous cross sectional thickness, which may increase stress risers in the prosthetic device 5, the resected bone of the femur 14, and the bone cement (if used for fixation).

In contrast to the embodiment of FIG. 5A and the embodiment of FIGS. 6A-6C, the inner surface 60 of the prosthetic device 5 may be configured so that the shapes of the first and second concave surfaces 62 and 64 are similar or identical. For example, as mentioned previously, FIG. 5B shows a cross sectional view of the prosthetic device 5 taken along the line D-D shown in FIG. 4C. In this embodiment, the prosthetic device 5 includes an inner surface 260 that corresponds to the inner surface 60 shown in FIGS. 4A-4F. The inner surface 260 includes a bone-engaging first concave surface 262 and a bone-engaging second concave surface 264. In this embodiment, the cross section at the first concave surface 262 and the cross section at the second concave surface 264 both have a semi-elliptical shape. Thus, the cross section of the inner surface 260 has a substantially elliptical (or oval) shape. One advantage of this embodiment is that it permits less bone resection on both the superior and inferior aspects 14a and 14b of the femoral head 16, which may be desirable because the femoral neck 18 is generally wider in the superior/inferior direction than in the anterior/posterior direction. One drawback, however, is that the embodiment of FIG. 5B (which includes a full ellipse) results in a prosthetic device 5 having even less material than the embodiment of FIG. 5A (which only includes a semi-ellipse). As a result, the embodiment of FIG. 5B may have diminished strength and stiffness. Although there may be situations where the embodiment of FIG. 5B is better suited to a specific patient's unique anatomical needs, in the majority of cases, the full ellipse configuration of FIG. 5B may be unnecessary given the relative lack of vascular structure near the inferior aspect 14b of the femur 14 and because the inferior portion of the femoral neck 18 is in compression during activities such as standing, walking, and running, and thus is less susceptible to fracture caused by femoral notching.

Additionally, although the above-described embodiments contemplate elliptical and circular curves, the present invention is not limited to such curves. The shape of the inner surface 60 of the prosthetic device 5 may include any curve (concave or convex) that is useful for conforming the shape of the inner surface 60 to the shape of a natural or prepared (i.e., sculpted) femoral head 16 and may also include one or more straight portions. Further, the shape of the inner surface 60 is not limited in the number, combination, or configuration of curves and straight portions that may be included. The inner surface 60 may also include other features, such as recesses (e.g., cement channels) and/or projections (e.g., for fixation or rotational alignment), which are known in the art. Additionally, the design of the prosthetic device 5 (including the shape of the inner surface 60) may be custom tailored to the patient's specific anatomy and disease state. For example, using appropriate software (such as IFIT software available from ConforMIS, Inc.) a surgeon can design a prosthetic device 5 that is configured to replace only those portions of the bone affected by disease while retaining healthy bone. As a result, the shape of the inner surface 60 may be customized to precisely match the patient's individual anatomy.

As shown in FIG. 4A, the prosthetic device 5 may include a stem 55 projecting from the inner surface 60 to aid in stability and initial fixation. The stem 55 may be formed integrally with the prosthetic device 5 or manufactured separately and connected to the prosthetic device 5 via mechanical means, such as screw threads or a press fit, as is known in the art. The stem 55 may be coaxial with the axis H-H (as shown in FIGS. 4E and 4F) or offset from the axis H-H (as disclosed, for example, in U.S. Patent Application Pub. No. US 2003/0163202, which is hereby incorporated by reference herein in its entirety). Inclusion of the stem 55 on the prosthetic device 5 is optional. One reason the stem 55 may be omitted is because the bone preparation process for the prosthetic device 5 does not utilize a cylindrical reamer. As explained above in connection with FIG. 3A, use of a cylindrical reamer requires the surgeon to create a guide hole G in the femoral head 16 to center the reamer 30. The guide hole G is then filled by the stem 32a of a conventional femoral hip resurfacing implant (as shown in FIGS. 3B and 3C). Because the present invention does not involve the use of cylindrical reamer to prepare the bone, a guide hole and a stem to fill the guide hole are not necessary for bone preparation. It may be desirable, however, to retain the stem 55 to ensure proper bone fixation or stress transfer to the bone or to ease placement of the implant on the bone.

The inner surface 60 of the prosthetic device 5 may be designed to be fixed to the femur 14 in any known manner. For example, the prosthetic device 5 may be adapted to be cemented in place with bone cement (e.g., polymethylmethacrylate or PMMA) or press fit onto the bone without cement. For cemented designs, portions of the inner surface 60 that will be cemented to the bone are preferably adapted to bond with the cement and may include cement pockets (e.g., shallow channels or circumferential grooves) to improve fixation, as is known in the art. Although the cement pockets may be formed on the inner surface 60 as concave channels, such cement pockets are different from the bone-engaging concave surfaces 62 and 64 discussed above. For example, cement pockets are designed to promote cementation, not to preserve critical anatomy. For press fit designs, uncemented portions of the inner surface 60 are preferably adapted to encourage the in-growth of bone to improve fixation. For example, such surfaces may be textured or roughened and/or may include a coating configured for bone in-growth, as is known in the art. The coating may be a porous coating, such as a sintered bead coating, a mesh coating, or plasma spray. Additionally or alternatively, the coating may be a bioactive coating, such as hydroxyapatite (HA).

The inner surface 60 of the prosthetic device 5 may also include other features adapted to promote fixation of the prosthetic device 5 to the femur 14. Such features may include one or more projections on the inner surface 60, such as pegs, spikes, fins, and the like, as known in the art. Such projections may be used with or without the stem 55. In one embodiment, the inner surface 60 includes a plurality of small projections (e.g., small, short pegs) and omits the larger and longer stem 55. Omission of the stem 55 in combination with a plurality of shallower fixation features advantageously provides fixation without significantly disrupting the internal vascular structures and bony anatomy of the femoral head 16.

As discussed above, the inner surface 60 and the outer surface 50 of the prosthetic device 5 are separated by the wall thickness t. As can be seen in FIGS. 4E, 5A, 5B, and 6C, the wall thickness t may be non-constant. This is because the shape of the outer surface 50 and the inner surface 60 do not have correspondence of shape and/or alignment. For example, the outer surface 50 may have a rotationally symmetric shape (e.g., a truncated spherical shape as shown in FIGS. 4A-4E) to promote joint articulation while the inner surface 60 may have a rotationally asymmetric shape (e.g., a shape that includes portions having different or varying curvatures as shown in FIGS. 5A, 5B, and 6A) to minimize intrusion on critical regions of anatomy. Alternatively, the shapes of the outer and inner surfaces 50 and 60 may correspond (e.g., both are substantially spherical) but may be offset from one another. For example, the outer surface 50 may be centered about the axis H-H while the inner surface 60 is centered about an axis that is offset from the axis H-H.

In one embodiment, a wall thickness of the first concave surface 62 is less than a wall thickness of the second concave surface 64. For example, in the embodiment of FIG. 4E, a wall thickness $t_1$ between the outer surface 50 and the first concave surface 62 is thinner than (i.e., less than) a wall thickness $t_2$ between the outer surface 50 and the second concave surface 64. As illustrated in FIG. 4E, the wall thicknesses $t_1$ and $t_2$ are taken at a plane M-M that is parallel to the plane T-T. Similarly, in FIG. 6C, a wall thickness $t_3$ between the outer surface 50 and the first concave surface 362 is thinner than a wall thickness $t_4$ between the outer surface 50 and the second concave surface 364. As illustrated in FIG. 6C, the wall thicknesses $t_3$ and $t_4$ are taken at a plane N-N that is parallel to the plane T-T. FIGS. 5A and 5B further illustrate exemplary variations in wall thickness of the prosthetic device 5. For example, in FIG. 5A, a wall thickness $t_5$ between the outer surface 50 and the first concave surface 162 is thinner than a wall thickness $t_6$ between the outer surface 50 and the second concave surface 164. In FIG. 5B, a wall thickness $t_7$ between the outer surface 50 and the first concave surface 262 is thicker than a wall thickness $t_8$ between the outer surface 50 and the second concave surface 264 and thicker than a wall thickness $t_9$ between the outer surface 50 and the first concave surface 262. One constraint on the design of the prosthetic device 5 is that the wall thickness t, which may be non-constant as described above, must still be sufficiently thick (even in the thinner regions) to avoid micromotion, metal fatigue, and deformation of the outer surface 50 of the prosthetic device 5. Additionally, the wall thickness t must be sufficiently robust to provide good stress transfer, avoiding stress shielding (which can lead to bone loss) and excessive stress.

The prosthetic device 5 may optionally include a cutout 67 to further reduce intrusion on critical regions of anatomy. As shown in FIGS. 4C-4E, in one embodiment, the cutout 67 is a raised portion created on the edge 52 of the prosthetic device 5. In a preferred embodiment, the cutout 67 coincides at least partially with the bone-conserving portion of the inner surface 60. For example, as shown in FIG. 4E, the cutout 67 coincides with a portion of the first concave surface 62 thereby reducing the surface area of the first concave surface 62. Because the cutout 67 reduces the surface area of the prosthetic device 5 that contacts the bone, the amount of bone that needs to be resected to install the prosthetic device 5 is reduced. For example, during surgical planning, the surgeon can plan the placement of the prosthetic device 5 on the patient's femoral head 16 such that the cutout 67 coincides with the vascular region 24. As a result, during surgery, the bone cuts in this region do not need to extend as far along the femoral neck 18 as they would if the cutout 67 was not present. This advantageously increases the distance between the bone cuts and the vascular region 24 resulting in improved preservation of critical structures, such as the retinacular vessels 24a, and reduced likelihood of femoral notching.

In one embodiment, the cutout 67 has an arcuate shape as shown in FIG. 4C. The cutout 67, however, is not limited in shape or size but instead may have any shape or size suitable for preserving one or more designated regions of anatomy without degrading the strength and stability of the prosthetic device 5. Additionally, the prosthetic device 5 may include multiple cutouts 67 as disclosed, for example, in U.S. Pat. No. 7,255,717, which is hereby incorporated by reference herein in its entirety.

The prosthetic device 5 may be made of any material suitable for use in orthopedic implant applications. For example, the prosthetic device 5 may include a biocompatible metal (e.g., a cobalt-chromium alloy, a titanium alloy, a zirconium alloy, stainless steel, or tantalum); a strong ceramic (e.g., an alumina or zirconia-based ceramic); one or more high performance polymers (e.g., UHMWPE); and/or a polymer composite. Additionally, selection of an appropriate material requires consideration of the specific design of the prosthetic device 5 (e.g., via finite element analysis, etc.) to ensure that the material has sufficient mechanical properties, in accordance with parameters known in the art. For example, in regions where the wall thickness t of the prosthetic device 5 is thin, a biocompatible metal may be more mechanically sound than a ceramic or polymer.

In operation, the prosthetic device 5 is implanted on the femur 14 of the patient after the surgeon has sculpted the femur 14 to receive the prosthetic device 5. To ensure that the prosthetic device 5 can be properly mated to the prepared femur 14, the femur 14 is preferably sculpted to have a surface shape that substantially corresponds to the rotationally asymmetric shape of the inner surface 60 of the prosthetic device 5. Because the shape of the sculpted bone will be rotationally asymmetric, the bone cannot be prepared using only conventional rotationally symmetric cutting tools, such as the cylindrical reamer 30 shown in FIG. 3A. Instead, the surgeon utilizes bone preparation techniques that enable the surface of the bone to be sculpted into a rotationally asymmetric shape, including convex surfaces that substantially correspond in shape and location to the concave surfaces of the inner surface 60. Because the inner surface 60 includes concave bone-conserving portions, sculpting corresponding convex surfaces into the bone enables the surgeon to avoid impingement of the cutting tool on critical regions of anatomy, such as the vascular region 24 and the femoral neck 18.

Various methods can be used to prepare the bone. For example, one method includes freehand sculpting where the surgeon uses a freehand technique to sculpt the bone with a high speed burring device. Freehand sculpting, however, is challenging and requires a high degree of surgical skill. In a true freehand technique, the surgeon sculpts the bone with the burr in an unaided manner. To improve execution of bone cuts, the surgeon can utilize mechanical guides, cutting jigs, and/or templates. Additionally or alternatively, the surgeon can use a tracked cutting tool and computer assisted surgery system that provides visual and/or audible guidance during cutting. The cutting tool could also be controlled to be retracted and/or disabled if the cutting tool is moved beyond a defined cutting boundary.

Another method of preparing the bone includes using an autonomous robotic system with a high speed burr to perform bone cuts automatically. Although such systems enable precise bone resections for improved implant fit and placement, they act autonomously and thus require the surgeon to cede a degree of control to the robot. Additional drawbacks include the large size of the robot, poor ergonomics, need to rigidly clamp the bone during registration and cutting, increased incision length for adequate robot access, and limited acceptance by surgeons and regulatory agencies due to the autonomous nature of the system.

Another method of preparing the bone includes using a haptically guided interactive robotic system, such as the haptic guidance system described in U.S. patent application Ser. No. 11/357,197 (Pub. No. 2006/0142657), filed Feb. 21, 2006, and hereby incorporated by reference herein in its entirety. As the surgeon manipulates a robotic arm to cut bone with a high speed burr, the system provides force feedback (i.e., haptic or tactile guidance) to guide the surgeon in sculpting the bone into the appropriate shape, which is pre-programmed into the control system of the robotic arm. In a preferred embodiment, the interactive robotic system is the TACTILE GUIDANCE SYSTEM™ currently manufactured by MAKO Surgical Corp., Fort Lauderdale, Fla.

Figure 7:
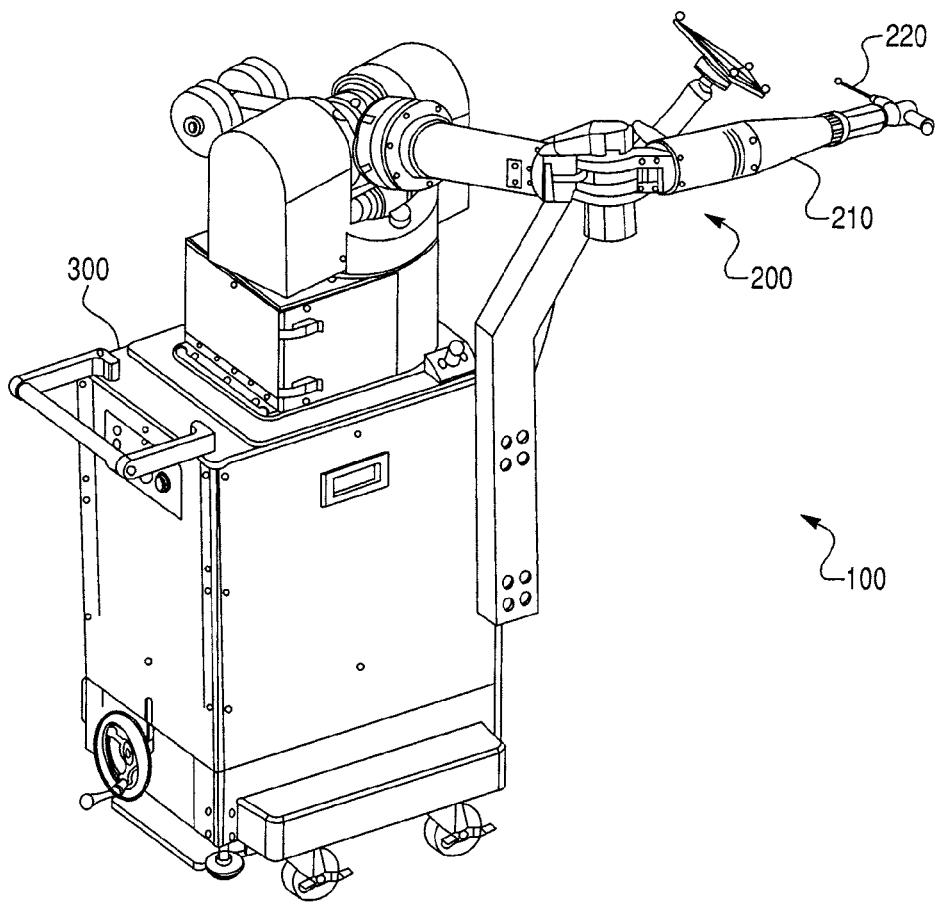
FIG. 7 is a perspective view of a surgical robotic system.

According to an exemplary embodiment, the femur 14 is prepared using a robotic system 100. In a preferred embodiment, the robotic system 100 is the haptic guidance system described in the above-referenced U.S. Patent Application Pub. No. 2006/0142657 or the TACTILE GUIDANCE SYSTEM™ currently manufactured by MAKO Surgical Corp., Fort Lauderdale, Fla. The robotic system 100 is adapted for preparing a bone of a joint to receive a substantially cup-shaped prosthetic device. For example, the robotic system 100 can be used to prepare the femur 14 of the hip joint 10 to receive the prosthetic device 5. As shown in FIG. 7, the robotic system 100 includes a controllable guide structure 200 and a control system 300 for controlling the guide structure 200.

The controllable guide structure 200 is configured to guide cutting of the bone into a shape for receiving the substantially cup-shaped prosthetic device (i.e., the prosthetic device 5). As shown in FIG. 7, the guide structure 200 comprises an articulated arm 210 with a distally mounted cutting tool 220 (e.g., a surgical burr). The guide structure 200 also incorporates a feedback mechanism (not shown) that includes a drive system comprising one or more actuators (e.g., motors) and a mechanical transmission. The feedback mechanism is configured to generate and convey force feedback to a user of the robotic system 100 to guide the user in making bone cuts. In operation, the surgeon cuts bone by grasping and manipulating the guide structure 200 (e.g., the arm 210 and/or the cutting tool 220) to make the desired bone cuts with the tool 220. During the cutting operation, the control system 300 controls the feedback mechanism to provide force feedback that guides the surgeon in executing the bone cuts. For example, the feedback mechanism may provide force feedback that tends to constrain the surgeon from penetrating a predefined virtual cutting boundary with the cutting tool 220. As discussed more fully below, the virtual cutting boundary may be defined by a bone-cutting pattern comprising a shape that corresponds to the rotationally asymmetric shape of the inner surface 60 of the prosthetic device 5. To enable the control system 300 to know the position of the bone-cutting pattern relative to the bone being cut, the bone-cutting pattern is registered to the patient's anatomy using any known registration technique. In this manner, the controllable guide structure 200 is configured to guide cutting of the bone (e.g., the femur 14) into a rotationally asymmetric shape. As a result, the prepared femur 14 and the prosthetic device 5 properly engage when the surgeon implants the prosthetic device 5 on the femur 14.

The control system 300 controls the robotic system 100, including the feedback mechanism of the guide structure 200. The control system 300 may be, for example, a computing system for controlling a haptic device as described in the above-referenced U.S. Patent Application Pub. No. 2006/0142657. To guide the surgeon in preparation of the bone, the control system 300 defines a virtual cutting boundary that is registered to the anatomy of the patient and then controls the feedback mechanism to provide force feedback to the surgeon to prevent the surgeon from making bone cuts that violate the virtual cutting boundary, as described, for example, in the above-referenced U.S. Patent Application Pub. No. 2006/0142657. The cutting boundary may be defined by a bone-cutting pattern programmed into the control system 300. For example, the bone-cutting pattern may be a haptic object or geometric model as described in the above-referenced U.S. Patent Application Pub. No. 2006/0142657. The bone-cutting pattern may be a single pattern that defines a final surface shape of the prepared bone or may comprise a plurality of patterns defining a plurality of bone cuts to be made to achieve the final surface shape. As discussed above, the shape of the bone-cutting pattern preferably substantially corresponds to the shape of the inner surface 60 of the prosthetic device 5 so that the bone is sculpted into a shape that can securely engage the prosthetic device 5. Thus, if the inner surface 60 is a rotationally asymmetric surface (as shown, for example, in FIGS. 4E and 5A), the bone-cutting pattern defines a rotationally asymmetric shape. During bone cutting, the control system 300 controls the feedback mechanism to provide force feedback guidance (e.g., haptic or tactile guidance) to the surgeon to enable the surgeon to maintain the cutting tool 220 within the cutting boundary defined by the bone-cutting pattern. As a result, the surface of the bone is sculpted into the shape defined by the bone-cutting pattern. Thus, when bone preparation is complete, the sculpted femur 14 will include convex portions that correspond in shape to the respective concave portions of the inner surface 60 of the prosthetic device 5.

Figure 8A:
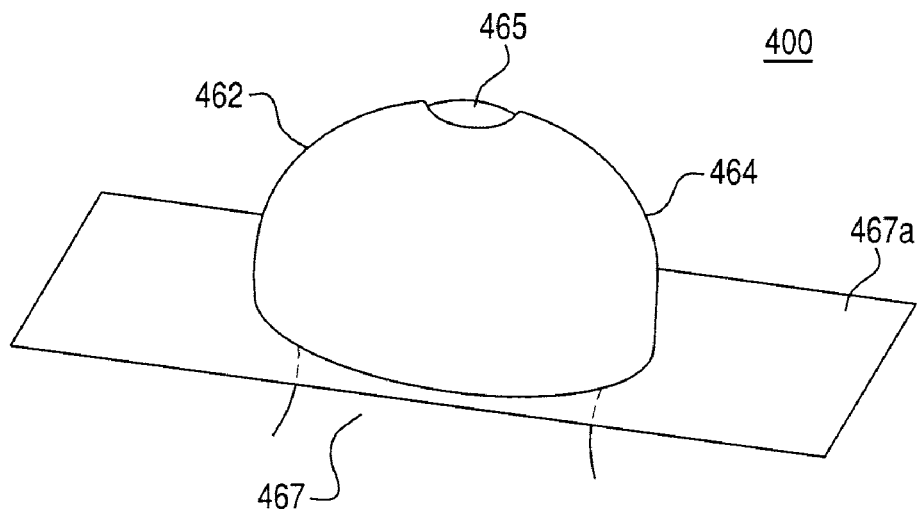
FIG. 8A is a perspective view of an embodiment of a bone-cutting pattern according to the present invention.
Figure 8B:
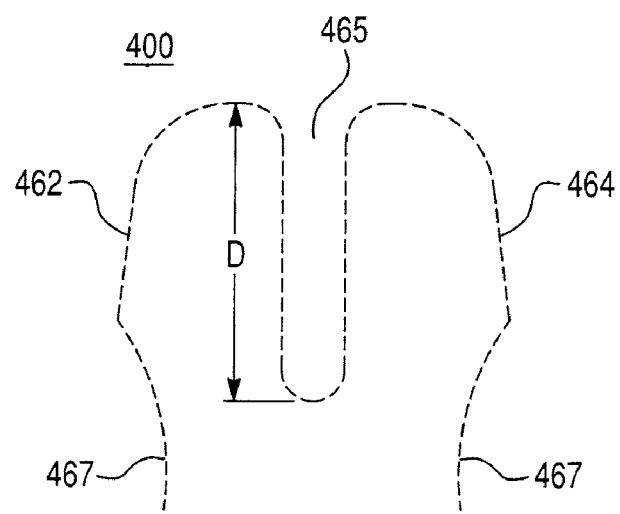
FIG. 8B is a cross sectional view of the bone-cutting pattern of FIG. 8A.

In one embodiment, the control system 300 includes at least one pre-defined bone-cutting pattern configured to reduce or minimize intrusion on a vascular region of the bone, such as the vascular region 24 of the femur 14. For example, FIG. 8A shows a bone-cutting pattern 400 that includes at least one bone-cutting pattern 462 for cutting a first convex surface 562 into a bone (i.e., the femur 14) and at least one bone-cutting pattern 464 for cutting a second convex surface 564 into the bone. The resulting convex surfaces 562 and 564 can be seen in FIG. 9, which illustrates a top view of the femur 14 sculpted using the bone-cutting pattern 400. If the prosthetic device 5 includes a stem 55, the bone-cutting pattern 400 may include a portion 465 defining an elongated channel to enable the surgeon to cut a corresponding channel in the bone to receive the stem 55. FIG. 8B, which is a cross sectional view of the bone-cutting pattern 400 taken through the geometric center of the portion 465, more clearly illustrates the portion 465, including a depth D of the elongated channel. Additionally, to prevent the surgeon from inadvertently notching the femoral neck 18 with the cutting tool 220, the bone-cutting pattern may include a protective region 467. In one embodiment, the protective region 467 is shaped similarly to but slightly larger than the patient's actual femoral neck 18. In this manner, the protective region 467 defines a virtual boundary that prohibits the surgeon from contacting the femoral neck 18 with the cutting tool 220. In another embodiment, the protective region may be configured to include an axial depth stop. For example, as shown in FIG. 8A, the protective region may include a plane 467a that corresponds to the plane T-T shown in FIG. 4E. In this embodiment, the plane 467a prevents the surgeon from cutting beyond the planned location of the edge 52 of the prosthetic device 5. In another embodiment (not shown), the protective region is similar to the plane 467a but includes a raised portion corresponding to the cutout 67 shown in FIG. 4E. In this embodiment, the surgeon's bone cuts are precisely constrained not to exceed a depth defined by the planned location and shape of the lower portion of the prosthetic device 5 (i.e., the edge 52 including the cutout 67). As will be apparent to one of skill in the art, the protective region is not limited to the above-described embodiments but may include any combination of shapes suitable to guide sculpting of bone while preserving critical anatomical structures. Additionally, the protective region may be dynamically modified throughout the course of the surgical procedure to provide the appropriate degree of guidance for each portion of the cutting operation, as described, for example in U.S. Pat. No. 7,206,626, which is hereby incorporated by reference herein in its entirety.

In the embodiment of FIGS. 8A and 8B, the bone-cutting pattern 400 is adapted to be used with the prosthetic device 5 shown in FIG. 5A. This prosthetic device 5 includes an inner surface 160 with a first concave surface 162 having a bone-conserving elliptical cross sectional shape and a second concave surface 164 having a circular cross sectional shape. Because the shape of the bone-cutting pattern 400 corresponds to the shape of the inner surface 160 of the prosthetic device 5, the bone-cutting pattern 400 also includes a circular portion and a bone-conserving elliptical portion. In particular, the pattern 462 of the bone-cutting pattern 400 corresponds to the elliptical surface 162 of the prosthetic device 5, and the pattern 464 corresponds to the circular surface 164 of the prosthetic device 5. As compared to the circular pattern 464, the elliptical shape of the pattern 462 reduces the amount of bone that must be resected. As a result, when the pattern 462 is positioned in the vicinity of the vascular region 24 of the femur 14, impingement of the cutting tool 220 on the vascular region 24 and the retinacular vessels 24a is reduced or minimized.

Figure 9:
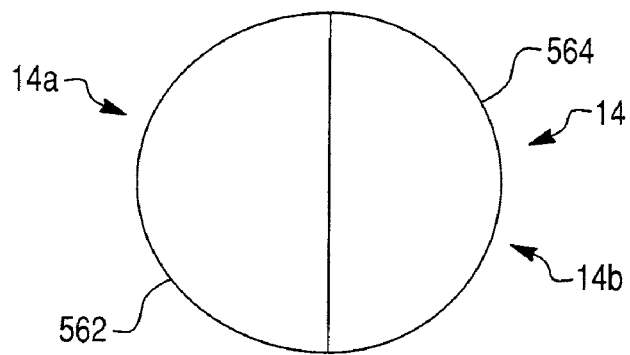
FIG. 9 is a top plan view of a femur sculpted using the bone-cutting pattern of FIG. 8A.

During cutting, the control system 300 controls the guide structure 200 to provide force feedback that enables the surgeon to accurately sculpt the femoral head 16 into the shape defined by the bone-cutting pattern 400. Thus, the controllable guide structure 200 is configured to guide cutting of the bone into a rotationally asymmetric shape using force feedback in combination with virtual cutting boundaries defined by the bone-cutting pattern 400. After cutting is complete, the sculpted convex surface 562 of the femur 14 has a bone-conserving elliptical shape, and the sculpted convex surface 564 has a circular shape, as shown in FIG. 9. The surgeon then implants the prosthetic device 5 on the femur 14 such that the elliptical concave surface 162 is aligned with the elliptical convex surface 562 of the sculpted femur 14. Similarly, the circular concave surface 164 of the prosthetic device 5 is aligned with the circular convex surface 564 of the sculpted femur 14.

In the above described embodiment, the bone-cutting pattern 400 produces bone cuts where a shape of the first convex surface 562 is different from a shape of the second convex surface 564 (e.g., an elliptical portion and a circular portion). Alternatively, the shape of the first and second convex surfaces 562 and 564 may be similar or identical. For example, the bone-cutting pattern may be configured to be used with the embodiment of the prosthetic device 5 shown in FIG. 5B such that the sculpted convex surfaces 562 and 564 of the bone each include elliptical portions. Additionally, as with the inner surface 60 of the prosthetic device 5, the shape of the bone-cutting pattern and the shape of the resulting sculpted surface of the bone are not limited to circular and elliptical curves but may include any curve (concave or convex) that is useful for conforming the shape of sculpted bone to the inner surface 60 of the prosthetic device 5 and may also include one or more straight portions. Further, the shape of the bone-cutting pattern and the shape of the resulting sculpted surface of the bone are not limited in the number, combination, or configuration of curves and straight portions that may be included. The bone-cutting pattern and the resulting sculpted surface of the bone may also include other features, such as recesses (e.g., cement channels) and/or projections.

The control system 300 may also be configured to permit the at least one predefined bone-cutting pattern to be modified based on the configuration of the bone to further minimize intrusion on the vascular region of the bone. For example, the control system 300 may be adapted so that the surgeon can modify the bone-cutting pattern preoperatively and/or intraoperatively to customize the bone-cutting pattern to the patient's unique anatomy, joint kinematics, and/or disease state. Thus, during surgery, if the surgeon notices that the vascular region 24 of the femur 14 is offset slightly from its expected location (e.g., as anticipated from preoperative CT scan data), the surgeon can modify the bone-cutting pattern to adjust the planned placement of the prosthetic device 5 relative to the femur 14. Similarly, if the surgeon discovers intraoperatively that the patient's bone is larger than was apparent from preoperative CT scan data, the surgeon can increase the size of the bone-cutting pattern to correspond to a larger prosthetic device 5. In cases where the design of the prosthetic device 5 is modified (e.g., preoperatively or intraoperatively) to be custom tailored to patient's specific anatomy (as discussed above), the bone-cutting pattern may be correspondingly modified.

Modifications may be accomplished in any known manner, such as by inputting information into the control system 300 so that the control system 300 (using appropriate software) can update the bone-cutting pattern. For example, if the bone-cutting pattern 400 (shown in FIG. 8) is stored in the control system 300 as a haptic object or geometric model, the surgeon can input data into the control system 300 indicating a desired modification, such as a change to the size, shape, and/or planned placement of the pattern 400 relative to the bone. The control system 300 can then modify the size, shape, and/or planned placement of the bone-cutting pattern 400 (i.e., the haptic object or geometric model), as described, for example, in the above-referenced U.S. Patent Application Pub. No. 2006/0142657. Thus, the surgeon has the flexability to modify the bone-cutting pattern as needed or desired.

The control system 300 may also be programmed to modify the bone-cutting pattern 400 automatically based, for example, on registration data and/or movement of the anatomy. For example, during surgery, if the registration process indicates that the patient's actual anatomy does not correspond to preoperative imaging data (e.g., CT scan data), the control system 300 can make appropriate changes to the bone-cutting pattern 400, such as increasing or decreasing the size of the pattern 400 and/or adjusting the planned alignment of the pattern 400 relative to the bone. Similarly, during surgery, if the control system 300 receives data (e.g., from a tracking system in communication with the control system 300) indicating that the bone (e.g., the femur 14) has moved or is moving, the control system can adjust the bone-cutting pattern 400 correspondingly so that the bone cuts made by the surgeon will be correct whether the patient is stationary or moving.

Figure 10:
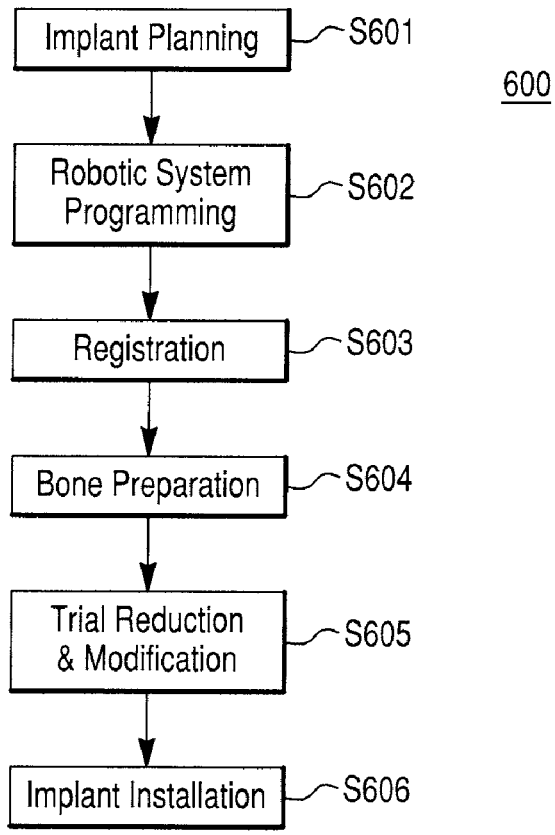
FIG. 10 is a diagram of an embodiment of a surgical method according to the present invention.

An embodiment of a surgical method 600 according to the present invention is illustrated in FIG. 10. In step S601 (Implant Planning), the surgeon selects a prosthetic device 5 to be implanted in the patient and plans where the prosthetic device 5 will be placed relative to the patient's anatomy. Implant planning may be accomplished preoperatively or intraoperatively and adjusted as necessary at any time. As is well-known, planning may be image-based or imageless in two or three dimensions (2D or 3D). For accuracy reasons, 3D image-based planning is preferred.

For 3D image-based planning, 3D images of the patient's bones are acquired using any suitable 3D imaging technology, such as CT, MRI, ultrasound, functional imaging, or other noninvasive or semi-invasive 3D imaging technology. The acquired image is processed using well known image processing techniques to generate 3D models of the bones of the joint. Alternatively, for 3D imageless planning, bone atlases may be used to obtain the 3D bone models. A bone atlas is a statistical model that represents the relevant anatomy, including information on natural variations typically existing in specific populations with specific distributions and probabilities. Using well known image processing techniques and statistical data, the bone atlas may be transformed or "morphed" to find a best fit to the patient's anatomy based on known demographic information, such as gender, age, stage of disease, and other patient-specific characteristics. Additionally, although preoperative planning can be accomplished using the initial bone atlas model, once intraoperative registration data on the actual bones is obtained, the bone atlas can be further morphed to improve the fit to the patient's anatomy along with corresponding adjustments to the implant plan.

After obtaining 3D bone models (image-based or imageless), the surgeon can use the models to plan placement of the prosthetic device 5 in the joint to achieve the desired clinical outcome. Various factors may be considered during implant planning, such as leg length, joint biomechanics, and joint kinematics, including range of motion, joint motion correction, impingement considerations, deformities, and the like. Implant planning may also take other factors into consideration, such as bone quality (e.g., measured using bone densitometry techniques), vascular structures in joint (e.g., the vascular region 24), existing necrotic tissue of the bone, prior joint trauma (including surgery), pre-existing implants, specific implant design features, and the like. Implant planning may be accomplished in any known manner, such as by manually positioning a virtual model of the implant (e.g., the selected prosthetic device 5) relative to the 3D model of the bone (e.g., the femur 14), as described in the above-referenced U.S. Patent Application Pub. No. 2006/0142657. The 3D nature of the application advantageously enables the surgeon to use simple image manipulation techniques to manually place implant components on the bone model, manipulate the implant components to obtain the appropriate position and alignment, and assess how the implant components will perform when installed in the joint.

An additional advantage of 3D image-based planning is the ability to analyze the level of damage and deformity of the diseased joint relative to itself as well as to the contralateral joint. For example, in the event the contralateral side is undamaged or in a reasonably healthy condition, the surgeon may consider the contralateral side as the goal for implant planning. For example, during implant planning, the surgeon can transpose an image of the healthy contralateral side to the image of the diseased side and use the healthy contralateral image as a reference target for planning implant placement.

In one embodiment, implant planning is accomplished by obtaining 3D bone models of the pelvis 12 and the femur 14. If only the femoral head 16 is being resurfaced, the surgeon plans the position of the prosthetic device 5 (i.e., the femoral component) on the model of the femur 14 (e.g., using the implant planning procedure described in the above-referenced U.S. Patent Application Pub. No. 2006/0142657). If the acetabulum 22 is also being resurfaced, the surgeon also plans the position of the acetabular component 28 on the model of the pelvis 12. Appropriate placement involves more than simply positioning models of the implant components on the bone models. As is well known, the surgeon must consider other factors, including the degree of post operative joint range of motion, whether the planned placement of the implants will result in proper leg length, and whether the thickness of the bone remaining in the acetabulum 22 after the acetabulum 22 is sculpted is structurally sufficient. For example, because the acetabulum 22 is relatively thin, placement of the acetabular component 28 should be as shallow as possible. Thus, in one embodiment, the position of the acetabular component 28 is planned first, and the position of the femoral component (e.g., the prosthetic device 5) is then planned to match the position of the acetabular component 28.

Positioning the prosthetic device 5 on the femoral head 16 should also take into account the patient's proper leg length. For example, if a patient has a healthy right hip joint and a left hip joint with a worn femoral head 16, the patient's left leg will be shorter than the right leg. Thus, when planning the placement of implant components in the left hip joint, the surgeon should ensure that the planned implant placement will achieve the correct leg length (i.e., the left leg should match the right leg). Because the patient's preoperative leg length is incorrect, however, proper leg length must be estimated. One way to estimate proper leg length is to align the patient's feet on the examination table and capture relative positions of the pelvis 12 and the femur 14. Another way to estimate leg length is to use the anatomically intact contralateral joint as mentioned above. Either approach should provide a nominal gap between the acetabulum 22 and the femoral head 16 that will result in comparable leg lengths. Implant placement can then be planned to achieve this nominal gap.

Alternatively, implant planning (or portions thereof) can be automated instead of manual. For example, 3D imaging in combination with programmable implant planning guidelines can enable a computer assisted surgery system to automatically plan the placement of implant components based on, for example, a recommended surgical technique, implant specific design, and/or patient joint condition. Once automatic planning occurs, the software can perform a virtual simulation of the joint in motion to provide the surgeon with information on joint kinematics and biomechanics as well as expected loads on the joint.

Figure 1B:
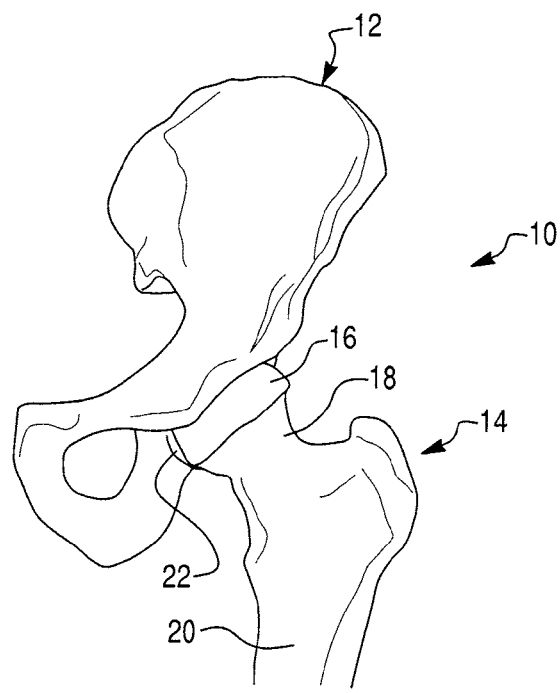
FIG. 1B is a perspective view of a hip joint formed by the femur and pelvis of FIG. 1A.
Figure 1C:
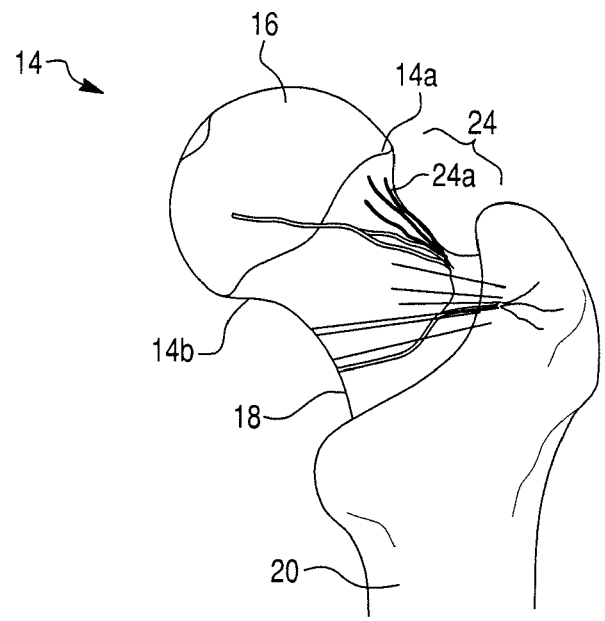
FIG. 1C is an illustration depicting a vascular region of a femur.

Although 3D imaging is preferred, 2D imaging may also be used. For example, as can be seen in FIGS. 1A and 1B, the hip joint 10 is a ball and socket joint with fairly simple anatomical shapes (as compared, for example, to a knee or ankle joint). The simple anatomy of the hip joint 10 combined with substantially symmetric geometry on the anterior/posterior plane for the femur 14 and substantially symmetric anatomy on the medial/lateral plane for the acetabulum 22 enables accurate planning of implant placement based on 2D images and implant models. The 2D implant planning process may utilize 2D templating techniques, as is well known. Alternatively, a 2D image may be used to find a best fit to an existing bone model, such as the bone atlas described above or other models representing the joint anatomy. For example, using well known image processing techniques, a computer can determine a best fit between 2D images of the patient's bone and the atlas and then morph the atlas to have a best fit to the specific information in the 2D image (e.g., size, shape, morphology, disease stage, etc.). Once the atlas is morphed to represent the specific patient anatomy, the atlas can be used to plan implant placement.

As described above, implant planning may be manual, automated, or a combination of manual and automated techniques. Additionally, implant planning may be performed preoperatively or intraoperatively and adjusted as necessary at any time. For example, a surgeon who chooses to plan implant placement preoperatively can make final adjustments to or even completely revise the plan intraoperatively after determining the actual condition of the joint. One disadvantage of preoperative planning, however, is that images of the patient must be acquired preoperatively and then registered to the actual patient during the surgical procedure. In contrast, with intraoperative planning, imaging is performed intraoperatively thereby avoiding the burden of preoperative imaging. Additionally, for certain imaging modalities, if the imaging apparatus is properly calibrated and both the imaging apparatus and the patient are tracked at the time the images are acquired, the acquired images are automatically registered with the patient. This eliminates the need for manual registration and thus results in a significant time savings for the surgeon. Any suitable known intraoperative imaging technology may be used, such as, for example, CT, ultrasound, 2D coordinated fluoroscopy, 3D fluoroscopy, and the like. As an alternative to intraoperative imaging, as is well known, the surface shape of the patient's bone may be mapped using a tracked probe, laser scanner, or other coordinate measuring device that can be inserted into an incision to capture points on the surface of the bone. The captured data is used to generate a cloud of points that can be used to reconstruct the surface of the bone or that can be fused to a bone model or bone atlas as described above.

One result of the implant planning process is that when the surgeon specifies the location of the selected prosthetic device 5 relative to the bone model, the position of the corresponding bone-cutting pattern relative to the bone model is known. This is because the bone-cutting pattern is linked to or associated with the model of the selected prosthetic device 5. In this manner, the appropriate bone-cutting pattern is registered to the model of the bone. As a result, the implant planning process defines the bone cuts that the surgeon needs to make to sculpt the femur 14 to receive the selected prosthetic device 5 in the planned position.

In step S602 (Robotic System Programming), the robotic system 100 is programmed with the implant planning data from step S601, including the model of the bone, the model of the selected prosthetic device 5, the bone-cutting pattern, and the planned implant placement. Alternatively, implant planning may be performed directly on a computing system associated with the robotic system 100 thereby eliminating step S602. Once the robotic system 100 receives the implant planning data, the robotic system 100 knows the location of the bone-cutting pattern relative to the model of the bone.

In step S603 (Registration), the controllable guide structure 200 of the robotic system 100 is registered to the patient using any known registration technique, such as the registration technique described in the above-referenced U.S. Patent Application Pub. No. 2006/0142657. During registration, the location of the patient's bone (i.e., the femur 14) in physical space is correlated to the model of the bone in virtual space. As a result of patient registration, the robotic system 100 knows the location of the patient's physical bone relative to the model of the bone. Thus, based on the implant planning data and the registration data, the robotic system 100 knows the location of the patient's physical bone relative to the bone-cutting pattern.

In step S604 (Bone Preparation), the surgeon manipulates the controllable guide structure 200 of the robotic system 100 to prepare the femur 14 with the cutting tool 220. During cutting, a tracking system in communication with the robotic system 100 tracks the location of the tool 220 and the femur 14 and, in most cases, allows the surgeon to freely move the cutting tool 220 in the surgical workspace. When the tool 220 is in proximity to a cutting boundary of the bone-cutting pattern, however, the control system 300 of the robotic system 100 controls the feedback mechanism to provide force feedback that tends to constrain the surgeon from penetrating the cutting boundary with the tool 220.

After bone sculpting is complete, in step S605 (Trial Reduction and Modification), the surgeon fits a trial implant to the prepared surface of the femur 14 and performs a trial reduction process to assess the fit of the trial implant. During this process, the surgeon can make any desired adjustments or modifications prior to installing the selected prosthetic device 5. Adjustments and modifications may include, for example, repeating implant planning, modifying the bone-cutting pattern, making additional bone cuts, selecting a different prosthetic device 5, and/or the like. When the surgeon is satisfied with the preparation of the femur 14 and the performance of the trial implant, in step S606 (Implant Installation), the selected prosthetic device 5 is installed on the femur and fixed in place, for example, via bone cement or a press fit.

The surgical method described is intended as an exemplary illustration only. In other embodiments, the order of the steps of the method may be rearranged in any manner suitable for a particular surgical application. Additionally, other embodiments may include all, some, or only portions of the steps of the surgical method and may combine the steps of the method with existing and/or later developed surgical approaches.

Thus, according to embodiments of the present invention, an orthopedic joint prosthesis and bone sculpting techniques that reduce or minimize intrusion on a vascular region of a bone are provided.

Other embodiments of the invention will be apparent to those skilled in the art from consideration of the specification and practice of the invention disclosed herein. It is intended that the specification and examples be considered as exemplary only.

What is claimed is:

1. A substantially cup-shaped prosthetic device for a joint, comprising:
    an outer surface configured to operatively engage at least one of a first bone of the joint and a component; and
    an inner surface configured to engage a second bone of the joint,
    wherein the inner surface is rotationally asymmetric such that an arc along the inner surface in a plane perpendicular to a longitudinal axis of the inner surface has a non-constant radius of curvature, and
    wherein the prosthetic device is a femoral head cup.

2. The substantially cup-shaped prosthetic device of claim 1, wherein the inner surface includes a bone-engaging first concave surface and a bone-engaging second concave surface, and a shape of the first concave surface is different from a shape of the second concave surface.

3. The substantially cup-shaped prosthetic device of claim 1, wherein a cross-section of the inner surface has a substantially elliptical shape.

4. The substantially cup-shaped prosthetic device of claim 1, wherein a cross-section of the inner surface includes an elliptical arc.

5. The substantially cup-shaped prosthetic device of claim 4, wherein the cross-section of the inner surface includes a circular arc.

6. The substantially cup-shaped prosthetic device of claim 1, wherein the inner surface includes a bone-engaging first concave surface and a bone-engaging second concave surface, and a wall thickness at the first concave surface is less than a wall thickness at the second concave surface.

7. The substantially cup-shaped prosthetic device of claim 1, wherein a wall thickness of the prosthetic device is non-constant.

8. The substantially cup-shaped prosthetic device of claim 1, wherein the inner surface includes a bone-engaging first concave surface and a bone-engaging second concave surface, and the first concave surface is located on a portion of the inner surface that will abut a vascular region of the second bone.

9. A substantially cup-shaped prosthetic device for a joint, comprising:
    an outer surface configured to operatively engage at least one of a first bone of the joint and a component; and
    an inner surface configured to engage a second bone of the joint,
    wherein the inner surface is rotationally asymmetric such that an arc along the inner surface in a plane perpendicular to a longitudinal axis of the inner surface has a non-constant radius of curvature,
    wherein the inner surface includes a bone-engaging first concave surface and a bone-engaging second concave surface, and a shape of the first concave surface is different from a shape of the second concave surface, and
    wherein the prosthetic device is a femoral head cup.

10. The substantially cup-shaped prosthetic device of claim 9, wherein the first concave surface is located on a portion of the inner surface that will abut a vascular region of the second bone.

11. A substantially cup-shaped prosthetic device for a joint, comprising:
- an outer surface configured to operatively engage at least one of a first bone of the joint and a component; and
- an inner surface configured to engage a second bone of the joint,
- wherein the inner surface is rotationally asymmetric such that an arc along the inner surface in a plane perpendicular to a longitudinal axis of the inner surface has a non-constant radius of curvature,
- wherein the inner surface includes a bone-engaging first concave surface and a bone-engaging second concave surface, and a shape of the first concave surface is different from a shape of the second concave surface,
- wherein a wall thickness at the first concave surface is less than a wall thickness at the second concave surface, and
- wherein the prosthetic device is a femoral head cup.

12. The substantially cup-shaped prosthetic device of claim 11, wherein the first concave surface is located on a portion of the inner surface that will abut a vascular region of the second bone.

* * * * *